US00PP11300P

United States Patent [19]

Boeder

[11] Patent Number: Plant 11,300

[45] Date of Patent: Mar. 21, 2000

[54] CHRYSANTHEMUM PLANT NAMED 'CLEAGAR VZP1'

[75] Inventor: Mark Boeder, West Wittering, United Kingdom

[73] Assignee: Cleangro Limited, West Sussex, United Kingdom

[21] Appl. No.: 09/038,791

[22] Filed: Mar. 11, 1998

[51] Int. Cl.[7] ..... A01H 5/00

[52] U.S. Cl. ..... Plt./287

[58] Field of Search ..... Plt./287, 292

[56] References Cited

U.S. PATENT DOCUMENTS

| | | | |
|---|---|---|---|
| P.P. 8,607 | 2/1994 | VandenBerg | Plt./287 |
| P.P. 9,584 | 6/1996 | Fuess | Plt./287 |
| P.P. 10,212 | 1/1998 | Wain | Plt./287 |
| P.P. 10,213 | 1/1998 | Wain | Plt./287 |

*Primary Examiner*—Howard J. Locker
*Attorney, Agent, or Firm*—Christie, Parker & Hale, LLP

[57] ABSTRACT

A new plant variety of Chrysanthemum producing red/purple flowers.

1 Drawing Sheet

BACKGROUND OF THE INVENTION

The present invention is directed to a new and distinct variety of Chrysanthemum botanically classified as *Dendranthema grandiflora*. The varietal denomination of the new chrysanthemum is 'Cleagar VZP1'.

The female parent of the new variety is the variety known as 'Barbara' (U.S. Plant Pat. No. 8,607) and the male parent is an undistributed, unnamed seedling identified as G6-C5. The new variety has been asexually reproduced by vegetative cuttings in Ventura County, Calif. and the distinguishing characteristics are retained through successive generations of asexual reproduction.

SUMMARY OF THE INVENTION

'Cleagar VZP1' is pot type Chrysanthemum plant variety that produces red/purple flowers.

Comparison With 'Barbara'

'Cleagar VZP1' differs from 'Barbara' in having a larger flower with a more flat capitulum. Also, plants of the new variety are larger but less upright than 'Barbara'.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of October. 'Cleagar VZP1' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once ten days after planting which results in about 4 breaks per pinch. It has been observed that the shelf life of 'Cleagar VZP1' is about 29 days with the response time of about 7.5 weeks. No treatment with growth retardant is required. Useful growing conditions include night temperatures of about 64°–66° F., day temperatures of about 80°–85° F. and about 5,000 foot-candles of light.

Plant:

- *Habit.*—Mounding.
- *Height.*—About 21 cm.
- *Number of breaks from pinch.*—About 4.
- *Typical container sizes commercially grown in.*—4 inch, 6 inch, 1 gallon, 3 gallon containers.
- *Length of lateral branches.*—About 17 cm.
- *Stem color.*—Near 147 C.

Foliage:

- *Leaf arrangement.*—Alternate.
- *Number of leaves per lateral branch.*—About 16.
- *Leaf size.*—Length: About 6.5 cm. Width: About 3.8 cm.
- *Leaf shape.*—Ovate.
- *Attachment.*—Petioled.
- *Leaf apex.*—Obtuse with serration at tip.
- *Base.*—Tapered.
- *Margin.*—Lobed, serrate.
- *Aspect.*—Undulate.
- *Surface.*—Top: Highly pubescent. Bottom: Highly pubescent.
- *Petiole length.*—About 1.8 cm. Color: Near 143 C.
- *Color.*—Mature leaf: Top: Near 147 A. Bottom: Near 137 C. Young leaf: Top: Near 137 B. Bottom: Near 137 C.

Flower:

- *Inflorescence form.*—Cyme.
- *Flower form.*—Decorative.
- *Number of blooms per branch.*—About 13.
- *Diameter of fully expanded bloom.*—About 4.5 cm.
- *Depth of fully expanded bloom.*—About 2 cm.
- *Sepal number.*—About 25. Color: Near 137 A.
- *General appearance of sepals.*—Highly membraneous.
- *Peduncle.*—Length: Lower most peduncle is about 7 cm, uppermost peduncle is about 3–4 cm, peduncle length increases progressing downward on the stem. Habit: Straight. Surface: Highly pubescent. Strength: Very sturdy.
- *Flower bud shape.*—Flattened sphere. Diameter: About 0.8 cm. Height: About 0.5 cm.
- *Ray florets.*—Number per flower: About 200. Shape: Elliptic, fused at base. Apex: 4 irregular lobes. Base: Tapered. Margin: Entire. Aspect: Undulating widthwise. Length: About 2.2 cm. Width: About 0.7 cm.

*Disc florets*.—Number per flower: About 10. Shape: Cylindrical. Length: About 0.5 cm. Width: About 0.08 cm.

*Fragrance*.—None.

Flower color:

*General flower coloration*.—Red/purple.

*Ray florets, top side*.—Immature: Near 70A. Mature: Near 64A. Fading: Near 60D.

*Ray floret, under side*.—Immature: Near 70B. Mature: Near 64A. Fading: Near 59D.

*Disc florets*.—Mature: Near 16A.

*Changes as the flower ages*.—Color fades, flower form remains very flat.

Reproductive organs:

*Ray florets*.—Pistillate. Stigma shape: 2 branched. Stigma color: Near 7A. Style length: About 0.4 cm.

*Disc florets*.—Stigma shape: Linear. Stigma color: Near 2C. Style length: About 0.2 cm. Stamen number: About 5. Anther length: About 0.1 cm. Pollen color: Near 20A. Pollen quantity: Minimal.

What is claimed is:

1. A new and distinct Chrysanthemum plant of the variety substantially as herein shown and described.

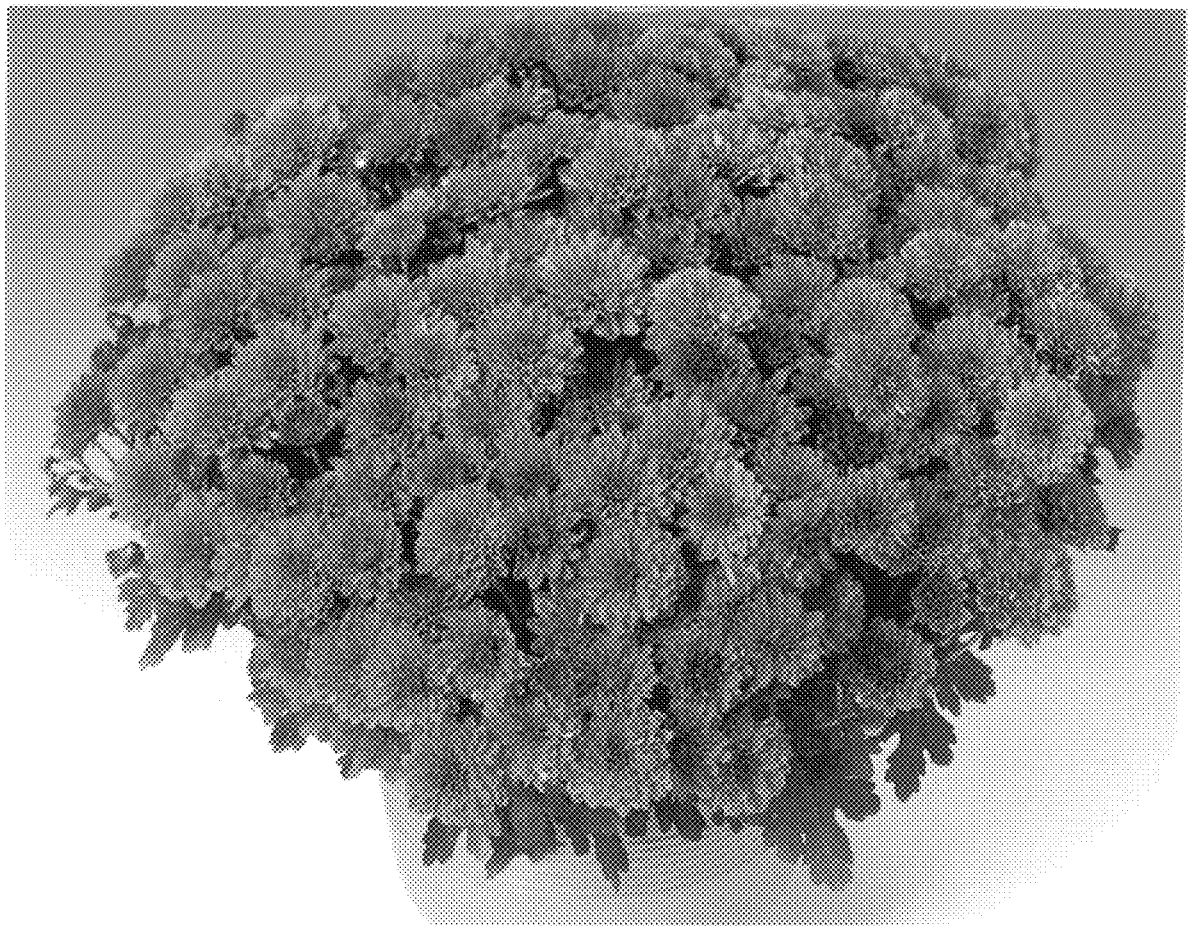

* * * * *